United States Patent [19]

Lawlis

[11] Patent Number: 5,020,520

[45] Date of Patent: Jun. 4, 1991

[54] THERAPEUTIC DEVICE FOR TREATING BACK PAIN

[76] Inventor: G. Frank Lawlis, 405 San Sebastai, Denton, Tex. 76205

[21] Appl. No.: 341,915

[22] Filed: Feb. 24, 1989

[51] Int. Cl.[5] .................................... A61F 5/00

[52] U.S. Cl. .................................... 128/71; 128/74

[58] Field of Search ............ 128/24 R, 33, 32, 34–39, 128/70–75, 24.3, 44–52, 56, 57

[56] References Cited

U.S. PATENT DOCUMENTS

| | | | |
|---|---|---|---|
| 1,194,939 | 8/1916 | Bishop | 128/73 |
| 1,989,434 | 1/1935 | Thompson | 128/73 |
| 2,091,014 | 8/1937 | Saak | 128/73 |
| 2,381,922 | 8/1945 | Norris | 128/73 |
| 2,786,512 | 3/1957 | Moyer | 128/71 |
| 3,589,358 | 6/1971 | Megal | 128/71 |
| 3,752,154 | 8/1973 | Clark | 128/33 |
| 3,380,233 | 8/1974 | Hill | 128/71 |
| 3,831,591 | 8/1974 | Newkirk | 128/33 |
| 3,835,844 | 9/1974 | Lang | 128/33 |
| 4,103,681 | 8/1978 | Shanley | 128/71 |
| 4,372,551 | 2/1983 | Yurdin | 128/70 |
| 4,494,260 | 1/1985 | Olds et al. | 128/33 |
| 4,574,785 | 3/1986 | Yamamoto | 128/24 R |
| 4,596,384 | 6/1986 | Blosser | 128/70 |
| 4,672,697 | 6/1987 | Schurch | 128/74 |
| 4,736,735 | 4/1988 | Yong | 128/41 |

*Primary Examiner*—Robert Bahr

*Attorney, Agent, or Firm*—Roylance, Abrams, Berdo & Goodman

[57] ABSTRACT

A therapeutic device for treating back pain and other related ailments in a patient includes a frame portion, a table portion, a leg support on the table portion and a tilting mechanism. The table portion is pivotably coupled at one end to the frame portion by a hinge. The leg support maintains the patient's legs in a bent position for properly positioning the patient to treat the patient's back. The tilting mechansim tilts the table portion to relieve minor compressional forces on the patient's back.

12 Claims, 2 Drawing Sheets

THERAPEUTIC DEVICE FOR TREATING BACK PAIN

FIELD OF THE INVENTION

The present invention relates to a therapeutic device for treating back pains in patients. In particular, the therapeutic device includes a table pivotably mounted at one end to a frame by a hinge, a leg support and a tilting mechanism for tilting the table about the hinge.

BACKGROUND OF THE INVENTION

Presently, a device is needed that is specifically designed to treat back pain in patients. While treating back pain, it is important that the device or procedure not aggravate other conditions of the patient, such as hypertension and headaches.

One method of treating back pain is the inversion method disclosed in U.S. Pat. No. 4,672,697 to Schurch. The Schurch patent discloses a tilting table which may be tilted 120° and on which the patient is held by his ankles. The inversion method poses serious problems to people with high blood pressure, hypertension and headaches. Thus, inverting a patient can cause more harm than that treated by using such device.

Another method of treating patients with back pain involves a padded table that is vibrated at spaced locations. An example of this method is disclosed in U.S. Pat. No. 4,736,735 to Yong. The Yong patent discloses a back massager device having a table that is vibrated, a foot rest and a special pad. While vibrating tables are useful, they are limited to massaging only those areas of the patient's back where the vibrator is attached to the table.

SUMMARY OF THE INVENTION

Accordingly, an object of the present invention is to provide a device for treating back pain and other related ailments.

Another object of the present invention is to provide a device which reduces stress and relaxes the patient.

A further object of the present invention is to provide a device which improves the circulation of the patient's blood.

Yet another object of the present invention is to provide a device which relaxes the backbone (i.e., decompression of the spine) without causing serious harm to patients afflicted with hypertension and/or headaches.

A still further object of the present invention is to provide a therapeutic device that is relatively inexpensive and easy to manufacture and operate.

The foregoing objects are basically obtained by a therapeutic device for treating back pain and other related ailments. The therapeutic device includes a frame portion, a table portion, a leg support, a hinge and a tilting mechanism. The table portion has an upper surface, a lower surface, a first end and a second end. The leg support is coupled to the table between its first and second ends for supporting a patient's legs above the upper surface of the table. The hinge couples the first end of the table to the frame portion for pivotable movement therebetween. The tilting mechanism is coupled to the frame portion and the table portion for pivoting the table portion about the hinge.

Other objects, advantages and salient features of the invention will become apparent from the following detailed description, which, taken in conjunction with the annexed drawings, discloses a preferred embodiment of the invention.

BRIEF DESCRIPTION OF THE DRAWINGS

Referring to the drawings which form a part of this disclosure.

DETAILED DESCRIPTION OF THE INVENTION

Figure 1:
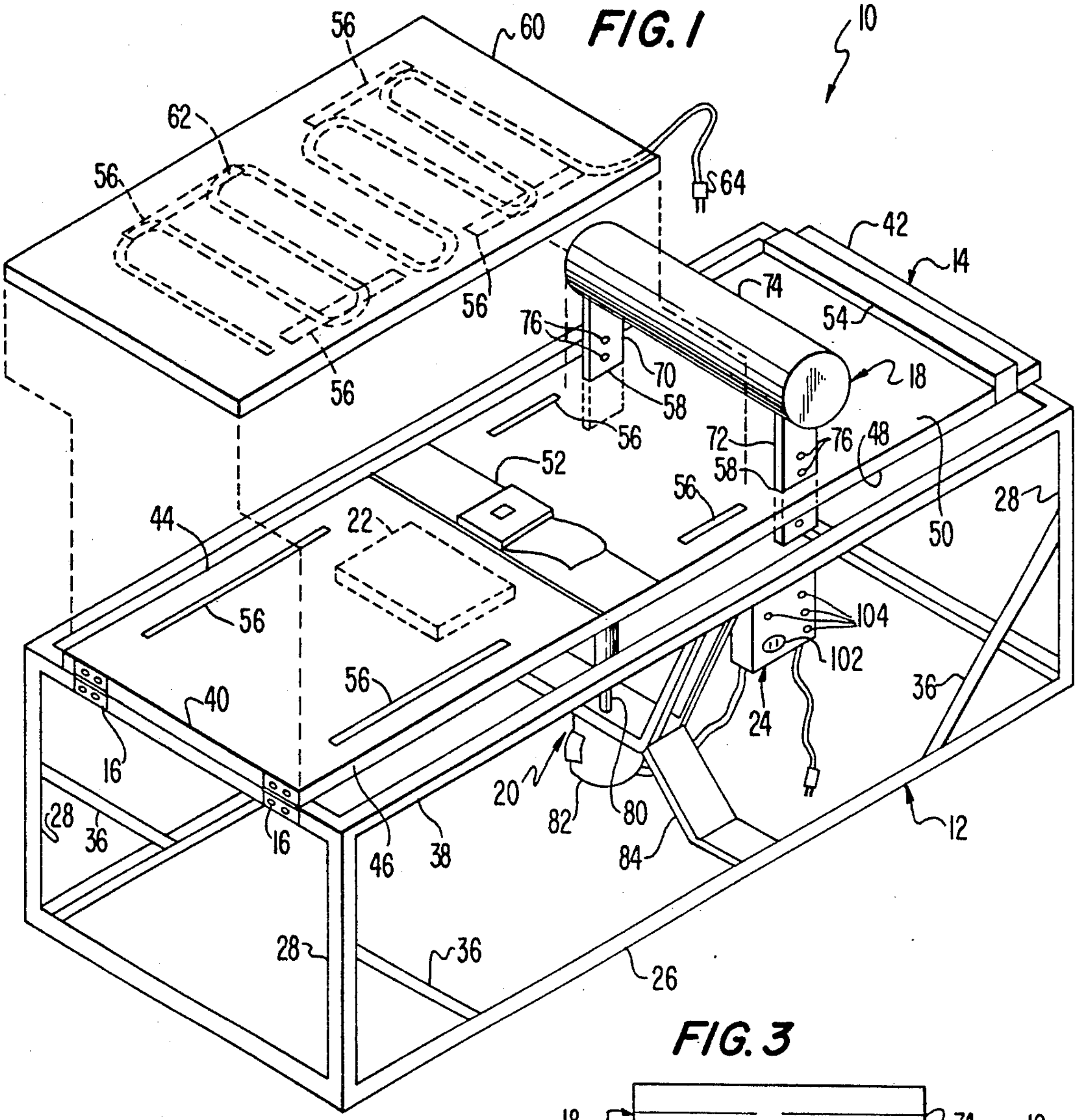
FIG. 1 is a perspective view of a therapeutic device with its heating pad exploded above the device in accordance with the present invention.

Referring initially to FIG. 1, a back pain machine or therapeutic device 10, in accordance with the present invention, includes a frame portion 12, a table portion 14, a pair of hinge members 16, a leg support 18, a tilting mechanism 20, a vibration mechanism 22, and a control mechanism 24.

Frame portion 12 includes a lower rectangular frame 26, four post members 28, four brace members 36 and an upper rectangular frame 38. Frame portion 12 is preferably made from one inch angle iron or other suitable materials, and is about 2.5 feet wide, about 6 feet in length and about 2 feet high. Post members 28 are rigidly coupled to lower frame 26 and upper frame 38 and extend generally perpendicularly therebetween at the corners of the upper and lower frames. Braces 36 are coupled at about 45° angles between post members 28 and the longitudinal sides of lower frame 26.

Table portion 14 is generally rectangular in shape and is about 2 feet wide, about 6 feet in length and about 1.5 inches thick. Any suitable material such as wood or a rigid plastic can be used to form the table portion. The table portion includes a first end 40, a second end 42, a first longitudinal side 44, a second longitudinal side 46, a lower surface 48, and an upper surface 50. A lap strap 52, a toe or foot strap 54, fastener strips 56 and a pad 60 are attached to table portion upper surface 50.

Lap strap 52 is attached about midway between and extends parallel to first end 40 and second end 42 of the table portion 14. Lap straps, such as lap strap 50, are well known in the industry, and thus, lap strap 50 is not illustrated or described in detail herein.

Toe or foot strap 54 is coupled adjacent and parallel to second end 42 of table portion 14. Toe strap 54 is preferably padded and coupled to table 14 in a conventional manner. Toe straps, such as toe strap 54, are well known in the industry, and thus, toe strap 54 is not illustrated or described in detail herein.

Fastener strips 56, preferably hook and loop fasteners (i.e., strips of VELCRO) engage and couple a heating pad 60 to table portion 14. The mating strips are on facing surfaces of the table portion and pad.

Pad 60 contains a heating element 62 with its plug 64 extending out of pad 60. Pad 60 can range in hardness and design, for example from a bumpy acupressure design to a soft sheepskin design. Also, heating element 62 is optional.

Hinge members 16 are coupled to first end 40 of table portion 14 and to the adjacent end of upper frame 38 for pivotally coupling table portion 14 to frame portion 12.

While two hinge members are shown, any number of hinges may be used as needed.

Figure 3:
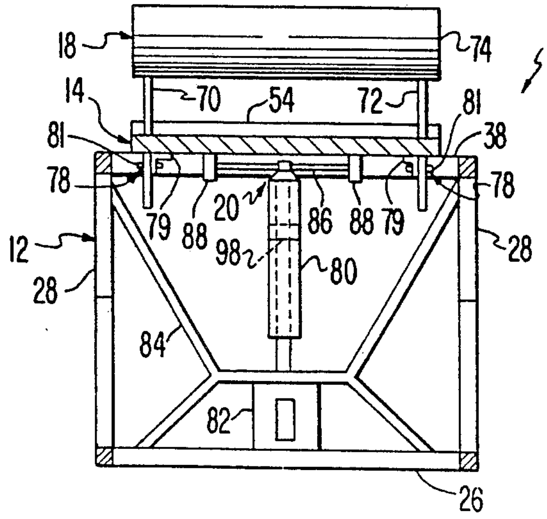
FIG. 3 is a transverse cross-sectional view taken along lines 3—3 of FIG. 2.
Figure 2:
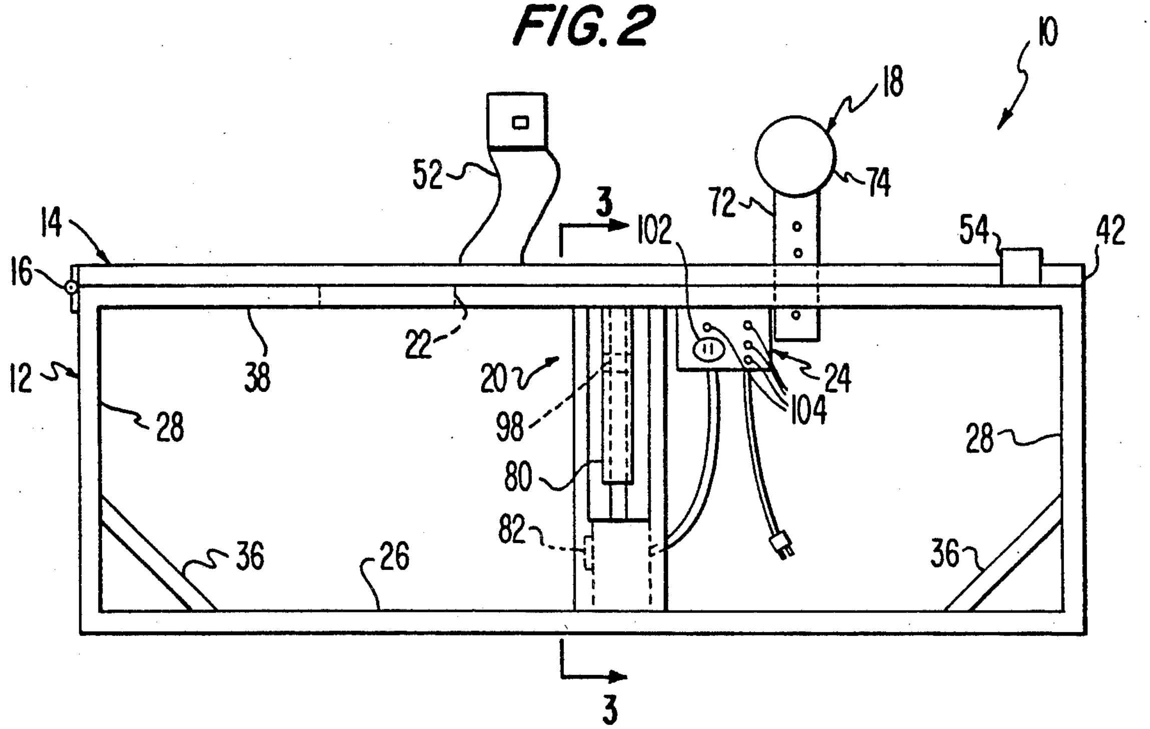
FIG. 2 is a side elevational view of the therapeutic device of FIG. 1 with its heating pad removed.

Leg support 18 includes a pair of extension members 70 and 72 and a padded cross bar 74 coupled between the upper ends of extension members 70 and 72. Padded cross bar 74 is preferably about 6 inches in diameter. Extension members 70 and 72 extend through rectangular holes 58 in table portion 14. Each extension member 70 and 72 has a plurality of holes 76 extending therethrough and spaced longitudinally along each extension member. Extension members 70 and 72 are adjustably coupled in height above upper surface 50 of table portion 14 by adjustment assemblies 78 coupled to lower surface 48 of table portion 14, as seen in FIG. 3. Adjustment assemblies 78 each include a bracket 79 rigidly coupled to table portion 14 and a bolt 81 extending through one of the holes 76 of one of the extension members and into a hole in bracket 79. Accordingly, leg support 18 can be adjusted by removing bolts 81 from one set of holes 76 in extension members 70 and 72 and inserting bolts 81 into another set of holes 76 in extension members 70 and 72.

When a patient is placed on the table portion, leg support 18 is located behind the patient's knees. This causes the patient to bend the patient's legs in the proper manner to enhance treatment of the back when relieving compression forces by tilting the table portion.

Figure 4:
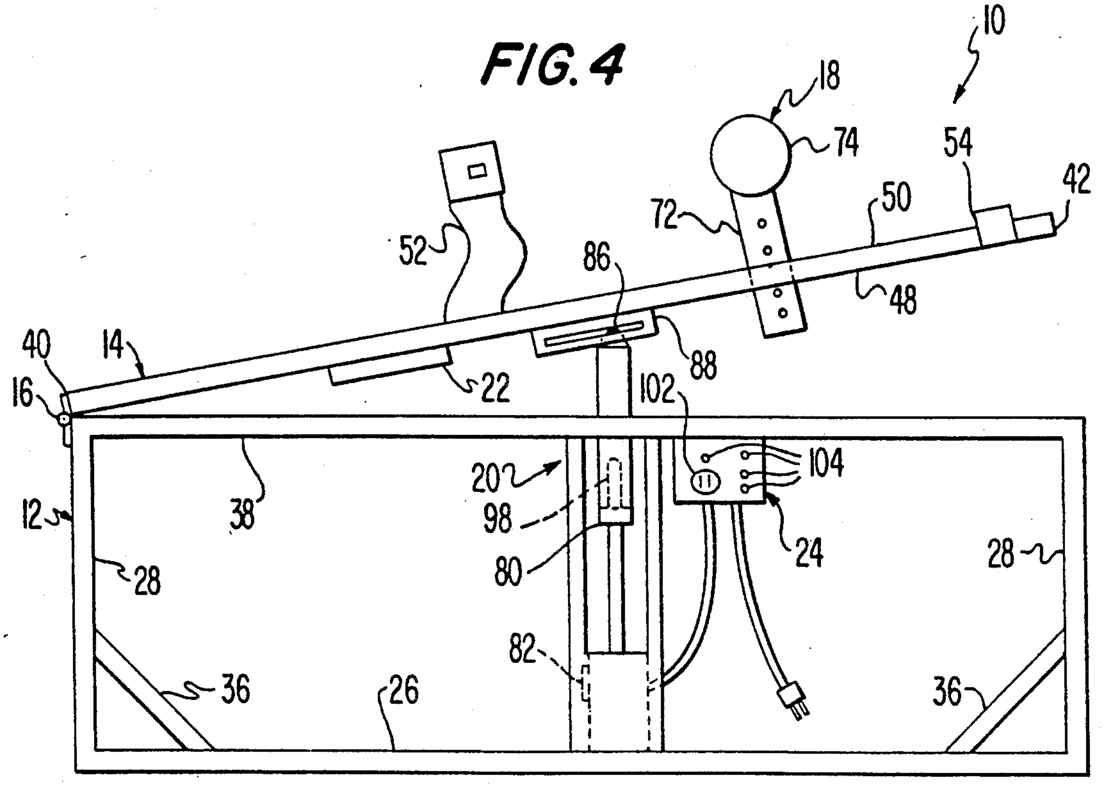
FIG. 4 is a side elevational view of the therapeutic device of FIG. 1 with its table portion elevated to about 20° and its heating pad removed.

Tilting mechanism 20 includes a jack 80, a motor 82, a support bracket 84, a connecting rod 86, and a pair of slotted brackets 88, as particularly seen in FIGS. 3 and 4. Support bracket 84 rigidly connects jack 80 and motor 82 to frame portion 12. Jack 80 is slidably connected to table portion 14 by connecting rod 86 and slotted brackets 88. Accordingly, upon extending jack 80, as seen in FIG. 4, table portion 14 is raised and connecting rod 86 slides along the slots in brackets 88.

Jack 80 can be a screw jack or a hydraulic jack, Motor 82 will be an electric motor or a hydraulic motor depending on the type of jack that is used.

Tilting mechanism 20 also should include a stopping member 98 for limiting the angle that table portion 14 may be tilted relative to frame portion 12. Preferably, table portion 14 should not be tilted more than about 20°.

Vibration mechanisms are well known in the industry and thus vibration mechanism 22 is not illustrated or described in detail herein. Vibration mechanism 22 is coupled to lower surface 48 of table portion 14 in a conventional manner.

Control mechanism 24 includes an outlet 102 and a plurality of control knobs or buttons 104. Control mechanism 24 is designed for controlling vibration mechanism 22, heating element 62 when plugged into outlet 102, tilting mechanism 20 and other options as desired.

While only one embodiment has been chosen to illustrate the invention, it will be understood by those skilled in the art that various changes and modifications can be made therein without departing from the scope of the invention as defined in the appended claims.

What is claimed is:

1. A therapeutic device for treating a patient's pain and other related ailments, comprising:

a frame portion;

a table portion having an upper surface, a lower surface, a first end and a second end;

a leg support coupled to said table portion between said first and second ends for supporting a patient's legs above said upper surface of said table portion, said leg support being spaced from said second end for engaging substantially beneath a patient's knees to support the patient's knees in a bent position, said leg support including means for adjusting to fix said leg support relative to said table portion at various spaced distances above said upper surface of said table portion;

hinge means for pivotably connecting said first end of said table portion to said frame portion; and tilting means, coupled to said frame portion and said table, for pivoting said table portion and said leg support simultaneously about said hinge means.

2. A therapeutic device according to claim 1, wherein said table portion comprises:

restraining means for holding the patient on said table portion.

3. A therapeutic device according to claim 2, wherein said restraining means comprises a foot strap.

4. A therapeutic device according to claim 3, wherein said restraining means further comprises a lap strap.

5. A therapeutic device according to claim 1, further comprising:

vibrating means, coupled to said lower surface of said table, for imparting, vibrational forces along said table portion.

6. A therapeutic device according to claim 1, wherein pad means is coupled to said upper surface of said table portion for cushioning said table portion.

7. A therapeutic device according to claim 6, wherein said pad means includes a heating element therein.

8. A therapeutic device according to claim 1, wherein said tilting means includes a screw jack fixedly coupled to said frame portion and slidably coupled to said lower surface of said table portion.

9. A therapeutic device according to claim 1, wherein said tilting means includes a hydraulic jack fixedly coupled to said frame portion and slidably coupled to said lower surface of said table portion.

10. A therapeutic device according to claim 1, wherein said tilting means includes a stop means for limiting the amount said table portion can be tilted relative to said frame portion.

11. A therapeutic device according to claim 10, wherein said stop means prevents said table portion from tilting more than 20°, relative to said frame portion.

12. A therapeutic device for treating a patient's back pain and other related ailments, comprising:

a frame portion;

a table portion having an upper surface, a lower surface, a first end and a second end;

a leg support coupled to said table portion between said first and second ends for supporting a patient's legs above said upper surface of said table portion, said leg support having means for adjusting to fix said leg support relative to said table portion at various spaced distances above said upper surface of said table portion, said leg support being spaced from said second end for engaging substantially beneath a patient's knees to support the patient's knees in a bent position;

hinge means for pivotably connecting said first end of said table portion to said frame portion;

tilting means, coupled to said frame portion and said table, for pivoting said table portion and said leg support simultaneously about said hinge means; and restraining means for holding the patient on said table portion, said restraining means includes a foot strap and a lap strap, said foot strap being adjacent to said second end of said table portion.

* * * * *